US010959800B2

(12) United States Patent
Cabrera

(10) Patent No.: US 10,959,800 B2
(45) Date of Patent: Mar. 30, 2021

(54) FORCE SENSORS FOR SURGICAL DEVICES TO PREVENT INGRESS OF FLUIDS

(71) Applicant: Covidien LP, Mansfield, MA (US)

(72) Inventor: Ramiro Cabrera, Cheshire, CT (US)

(73) Assignee: COVIDIEN LP, Mansfield, MA (US)

( * ) Notice: Subject to any disclaimer, the term of this patent is extended or adjusted under 35 U.S.C. 154(b) by 611 days.

(21) Appl. No.: 15/797,064

(22) Filed: Oct. 30, 2017

(65) Prior Publication Data

US 2018/0125601 A1 May 10, 2018

Related U.S. Application Data

(60) Provisional application No. 62/418,995, filed on Nov. 8, 2016.

(51) Int. Cl.
*A61B 90/00* (2016.01)
*A61B 17/115* (2006.01)
(Continued)

(52) U.S. Cl.
CPC ........ *A61B 90/06* (2016.02); *A61B 17/00234* (2013.01); *A61B 17/10* (2013.01); *A61B 17/115* (2013.01); *A61B 17/1155* (2013.01); *A61B 34/76* (2016.02); *G01L 1/2231* (2013.01); *G01L 5/0061* (2013.01); *G01L 5/22* (2013.01); *A61B 2017/00398* (2013.01); *A61B 2017/07257* (2013.01); *A61B 2090/064* (2016.02); *A61B 2090/065* (2016.02)

(58) Field of Classification Search
CPC ............ A61B 2562/16; A61B 2562/18; A61B 2090/064; G01L 1/2287; G01L 1/2206; G01L 1/2231
See application file for complete search history.

(56) References Cited

U.S. PATENT DOCUMENTS 5,052,505 A * 10/1991 Naito ................... G01G 3/1412
177/229
2013/0014595 A1 1/2013 Huizinga et al.
(Continued)

FOREIGN PATENT DOCUMENTS

| CN | 102274060 A | 12/2011 |
|----|-------------|---------|
| DE | 2924503 A1 | 1/1981 |
| WO | 2008067392 A2 | 6/2008 |

OTHER PUBLICATIONS

Extended European Search Report corresponding to counterpart Patent Appln. EP 17 20 0327.9 dated Apr. 5, 2018.
(Continued)

*Primary Examiner* — Erika J Villaluna

(57) ABSTRACT

A force sensor includes a substrate, a plurality of sensing elements, a seal, and a cover plate. The substrate includes a proximal surface and a distal surface, with the plurality of sensing elements coupled to the distal surface of the substrate. The seal includes a base wall and a flange extending proximally from the base wall. The flange is positioned against the distal surface of the substrate to define a cavity between the base wall of the seal and the distal surface of the substrate within which the plurality of sensing elements are disposed. The cover plate is positioned over the seal and fixed to the substrate. The cover plate applies a closure force on the seal to inhibit the ingress of fluids into the cavity.

19 Claims, 6 Drawing Sheets

(51) Int. Cl.
*G01L 1/22* (2006.01)
*A61B 34/00* (2016.01)
*G01L 5/00* (2006.01)
*A61B 17/00* (2006.01)
*A61B 17/10* (2006.01)
*G01L 5/22* (2006.01)
*A61B 17/072* (2006.01)

(56) References Cited

U.S. PATENT DOCUMENTS

2016/0296234 A1   10/2016  Richard et al.
2016/0310134 A1   10/2016  Contini et al.
2017/0172390 A1*  6/2017  Fu ............................ A61B 1/07
2017/0268938 A1    9/2017  Petersen et al.

OTHER PUBLICATIONS

Extended European Search Report dated Apr. 15, 2020 corresponding to counterpart Patent Application EP 20151534.3.
Chinese First Office Action dated Aug. 31, 2020 corresponding to counterpart Patent Application CN 201711084517.3.

* cited by examiner

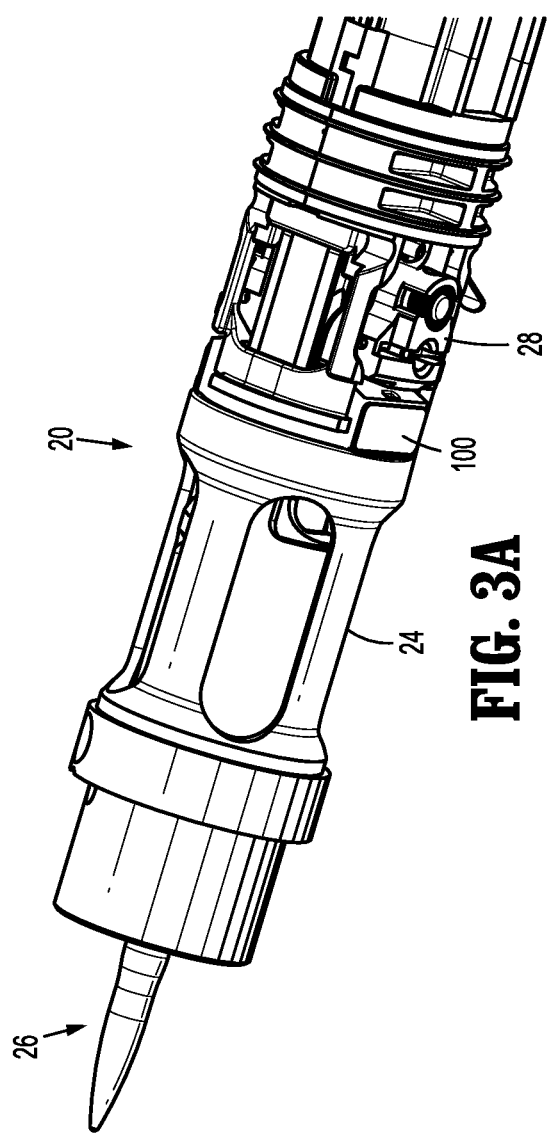
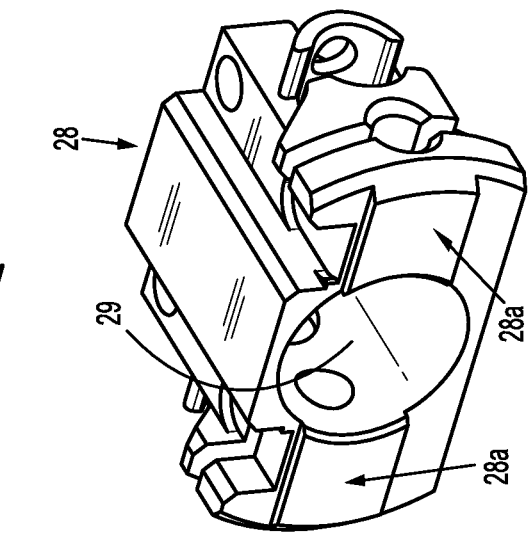
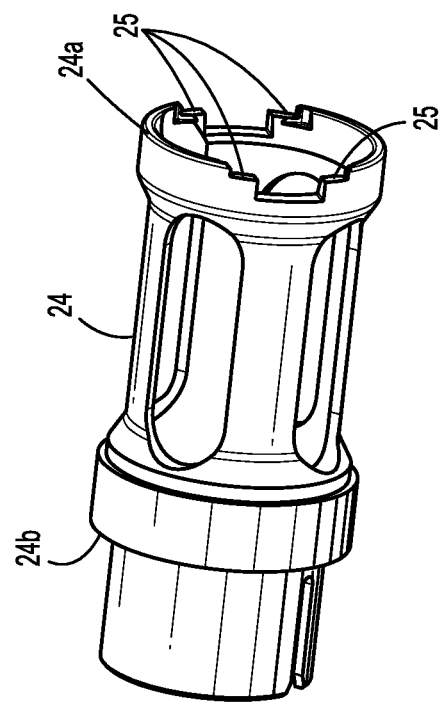
FIG. 3A
FIG. 3B
FIG. 3C

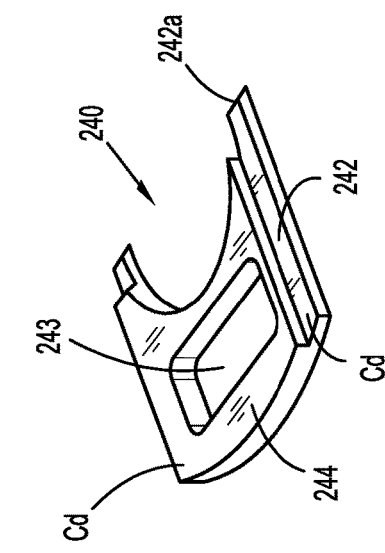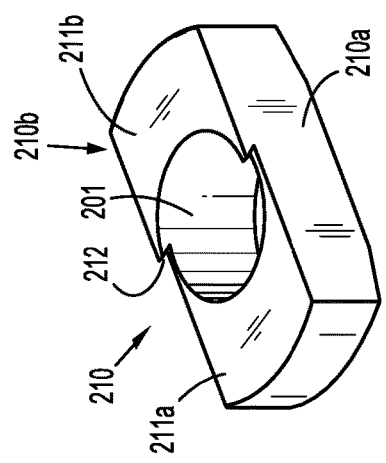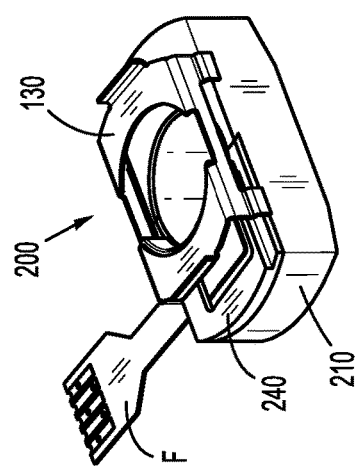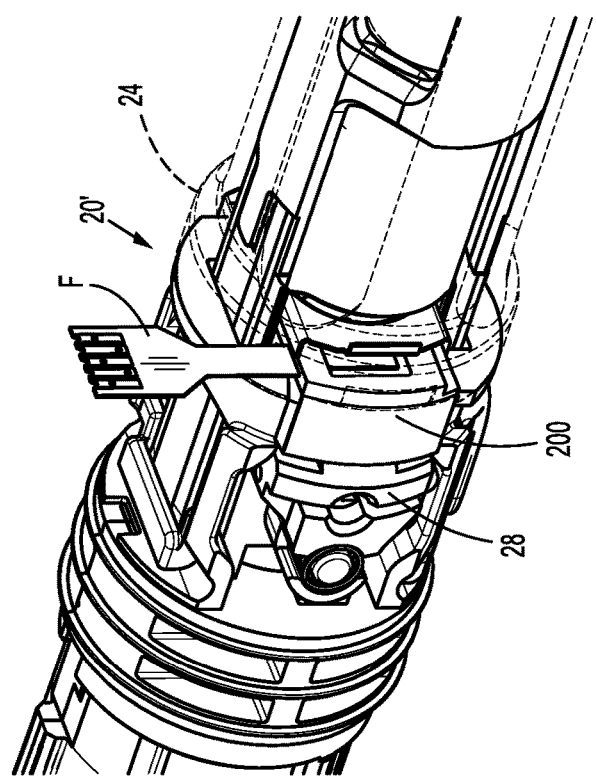

FORCE SENSORS FOR SURGICAL DEVICES TO PREVENT INGRESS OF FLUIDS

CROSS-REFERENCE TO RELATED APPLICATIONS

This application claims the benefit of and priority to U.S. Provisional Patent Application No. 62/418,995 filed Nov. 8, 2016, the entire disclosure of which is incorporated by reference herein.

TECHNICAL FIELD

The present disclosure relates generally to surgical devices. More particularly, the present disclosure relates to force sensors for powered surgical devices.

BACKGROUND

Force sensors (e.g., load reading sensors) have been used to enhance control of functions in a surgical device, such as a surgical stapling instrument. By using a force sensor, the clamping, stapling, and cutting forces of the surgical device can be monitored and used to regulate these various functions. The force sensor can be used to detect pre-set loads and cause the surgical device to react when those pre-set loads are reached. For example, during clamping of thick tissue, the load may rise to a pre-determined limit at which point the surgical device can slow clamping to control the clamping force as the tissue relaxes. This allows for clamping of thick tissue without damage to such tissue (e.g., serosa tears). One such example is the firing of a powered circular stapler type surgical device to create an anastomosis (e.g., an End-to-End Anastomosis (EEA) device). The intelligence of such a surgical device results in a higher product cost compared to currently available disposable units. Accordingly, it would be beneficial if such intelligent devices are reusable.

Reusable surgical devices must be cleaned (e.g., disinfected using high pH solutions) and sterilized prior to subsequent uses. The most common method of sterilization is the use of autoclaving. Autoclaving utilizes high pressure superheated steam (e.g., 37 PSI @ 137° C. for 18 minutes). Such an environment is known to damage various electronic components. For example, during autoclaving procedures, force sensors subjected to moisture at high temperature and high pressure may suffer from moisture ingress, thermal epoxy breakdown which may compromise the chemical bond of a sensing element (e.g., a strain gauge) to a substrate, and/or breakdown of the integrity of protective coatings. Thus, a need exists for force sensors that can withstand repeated high pH cleanings and sterilizations.

SUMMARY

The force sensors of the present disclosure are sealed and configured to withstand environmental stresses associated with high pH cleaning and sterilization (e.g., autowashing and/or autoclaving), minimizing and/or eliminating the ingress of fluids during such processes, thereby rendering the force sensors more durable for re-use.

In one aspect of the present disclosure, a force sensor includes a substrate, a plurality of sensing elements, a seal, and a cover plate. The substrate includes a proximal surface and a distal surface, with the plurality of sensing elements coupled to the distal surface of the substrate. The seal includes a base wall and a flange extending proximally from the base wall. The flange is positioned against the distal surface of the substrate to define a cavity between the base wall of the seal and the distal surface of the substrate within which the plurality of sensing elements is disposed. The cover plate is positioned over the seal and fixed to the substrate. The cover plate applies a closure force on the seal to inhibit the ingress of fluids into the cavity.

In embodiments, the seal is fabricated from a low durometer material. In some embodiments, the seal is fabricated from silicone.

The distal surface of the substrate may include first and second lateral halves, and the plurality of sensing elements may be disposed on the first lateral half of the distal surface. The seal may be sized and shaped to cover the first lateral half of the distal surface of the substrate. The cover plate may include a plate body having first and second lateral portions, the first lateral portion abutting the base wall of the seal.

In embodiments, the cover plate includes first and second rails extending proximally from the plate body, with the first and second rails operably seated adjacent first and second ledges, respectively, of the distal surface of the substrate. In some embodiments, the cover plate includes a plurality of legs engaged with side surfaces of the substrate.

A flex cable may be electrically coupled to the plurality of sensing elements and may extend between the seal and the distal surface of the substrate. In some embodiments, the seal includes a lip extending from the flange, and the first rail of the cover plate secures the lip against the first ledge of the distal surface of the substrate.

The seal may include a protrusion extending distally from the base wall of the seal, and the cover plate may include an opening engaged with the protrusion of the seal.

In embodiments, the force sensor is disposed between a distal connector housing and a trocar connection housing of an adapter assembly of a surgical device. The surgical device may include a powered handle assembly, the adapter assembly, and an end effector releasably secured to the distal connector housing of the adapter assembly. The force sensor may be configured to measure forces exhibited by the end effector along a load path.

In another aspect of the present disclosure, a force sensor includes a substrate, a plurality of sensing elements, a reservoir plate, and a cover plate. The substrate includes a proximal surface and a distal surface, with the plurality of sensing elements coupled to the distal surface of the substrate. The reservoir plate includes a main body and a raised central portion having an opening defined therethrough. The reservoir plate is mounted to the distal surface of the substrate, and the plurality of sensing elements is disposed within the opening and hermetically sealed therein. The cover plate is positioned over the reservoir plate and welded to the substrate.

In embodiments, the substrate includes first and second lateral halves interconnected by an intermediate wall, with the first lateral half having a lower height than the second lateral half. In some embodiments, the reservoir plate is welded to the first lateral half of the substrate, and the main body of the reservoir plate has a height that is equal to a height difference between the first and second lateral halves.

A sealant may be disposed over the plurality of sensing elements within the opening of the reservoir plate. Additionally or alternatively, a seal may be disposed over the reservoir plate. In embodiments, the seal includes a base wall and a flange disposed around the entire outer perimeter of the base wall and extending proximally therefrom. The flange may be positioned against the distal surface of the substrate to define a cavity in which the raised central portion of the reservoir plate is housed, and the cover plate applies a closure force on the seal to inhibit the ingress of fluids therein.

A flex cable may be electrically coupled to the plurality of sensing elements and may extend between the reservoir plate and the distal surface of the substrate.

In embodiments, the force sensor is disposed between a distal connector housing and a trocar connection housing of an adapter assembly of a surgical device. The surgical device may include a powered handle assembly, the adapter assembly, and an end effector releasably secured to the connector housing of the adapter assembly. The force sensor may be configured to measure forces exhibited by the end effector along a load path.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 3A is a perspective view of a distal end portion of the adapter assembly of FIGS. 1 and 2, with an outer sleeve of the adapter assembly removed therefrom;

FIG. 3B is an enlarged perspective view of a trocar connection housing of the adapter assembly of FIG. 3A;

FIG. 3C is an enlarged perspective view of a distal connector housing of the adapter assembly of FIG. 3A;

FIG. 7 is a perspective view of a force sensor in accordance with another embodiment of the present disclosure;

FIG. 8A is a perspective view of a substrate of the force sensor of FIG. 7;

FIG. 8B is a perspective view of a reservoir plate of the force sensor of FIG. 7; and FIG. 9 is a perspective view of a distal end portion of an adapter assembly of a surgical device including the force sensor of FIG. 7, with an outer sleeve of the adapter assembly removed therefrom and the distal connector housing shown in phantom.

DETAILED DESCRIPTION

Figure 1:
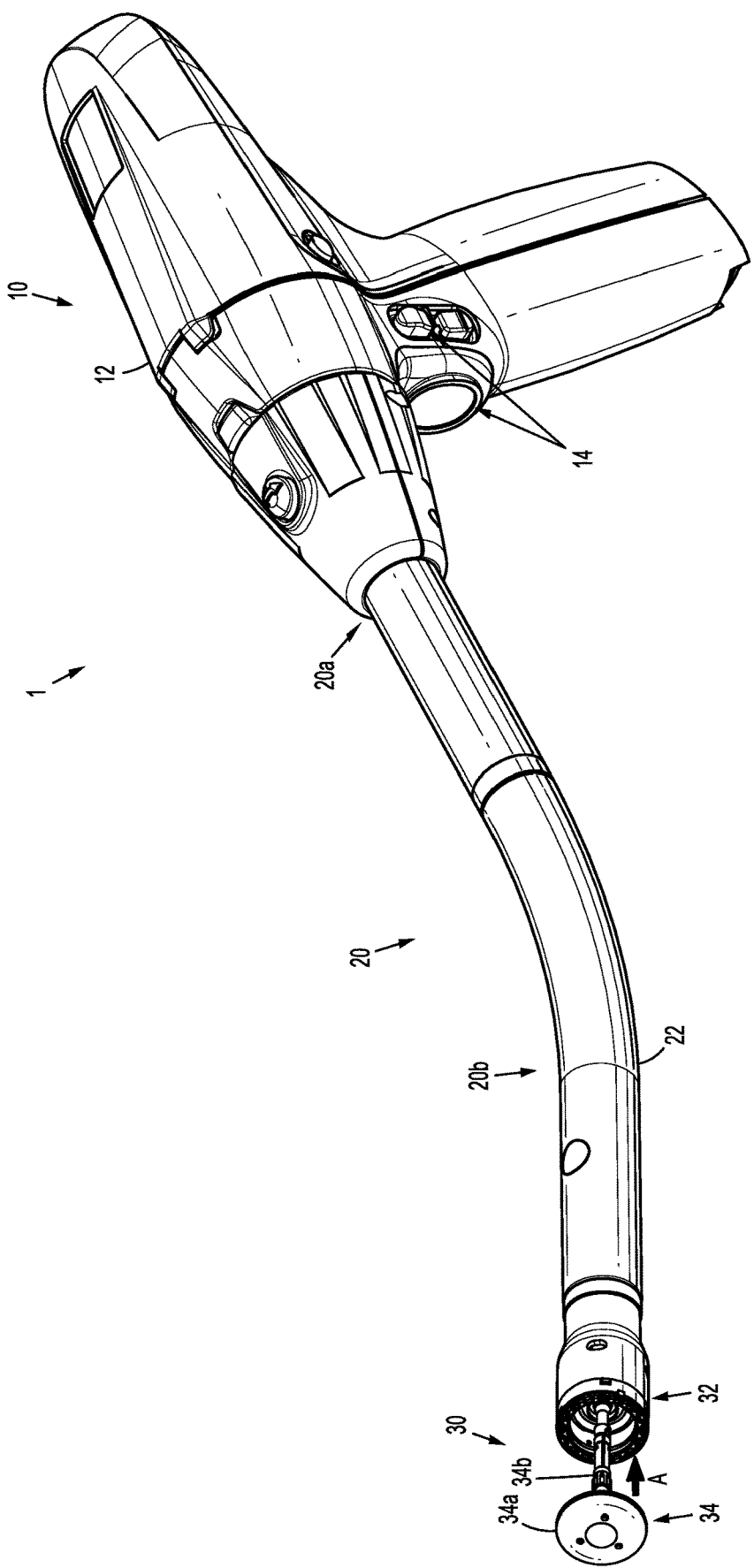
FIG. 1 is a perspective view of a surgical device in accordance with an embodiment of the present disclosure.

The force sensors of the present disclosure include sensing elements of, e.g., surgical devices, that are protected from harsh environments, such as autowashing and/or autoclaving. The force sensors include a substrate having sensing elements, such as strain gauges and their supporting electronics, mounted thereon, which are covered by seals and/or plates to create a protective leak-proof barrier to protect the sensing elements.

Embodiments of the present disclosure are now described in detail with reference to the drawings in which like reference numerals designate identical or corresponding elements in each of the several views. Throughout this description, the term "proximal" refers to a portion of a device, or component thereof, that is closer to a hand of a user, and the term "distal" refers to a portion of the device, or component thereof, that is farther from the hand of the user. Directional reference terms, such as "top," "bottom," "upper," "lower," and the like, are intended to ease description of the embodiments and are not intended to have any limiting effect on the ultimate orientations of the surgical devices, or any parts thereof.

Turning now to FIG. 1, a surgical device 1, in accordance with an embodiment of the present disclosure, is in the form of a powered handheld electromechanical instrument, and includes a powered handle assembly 10, an adapter assembly 20, and a tool assembly or end effector 30 including a loading unit 32 having a plurality of staples (not shown) disposed therein and an anvil assembly 34 including an anvil head 34a and an anvil rod 34b. The powered handle assembly 10 is configured for selective connection with the adapter assembly 20 and, in turn, the adapter assembly 20 is configured for selective connection with the end effector 30.

While described and shown as including adapter assembly 20 and end effector 30, it should be understood that a variety of different adapter assemblies and end effectors may be utilized in the surgical device of the present disclosure. For a detailed description of the structure and function of exemplary surgical devices, reference may be made to commonly owned U.S. patent application Ser. No. 14/991,157 ("the '157 application"), filed on Jan. 8, 2016, and Ser. No. 15/096,399 ("the '399 application"), filed on Apr. 12, 2016, the entire contents of each of which are incorporated herein by reference.

With continued reference to FIG. 1, the handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. For a detailed description of an exemplary handle assembly, reference may be made to the '399 application, the entire contents of which were previously incorporated herein by reference.

Figure 2:
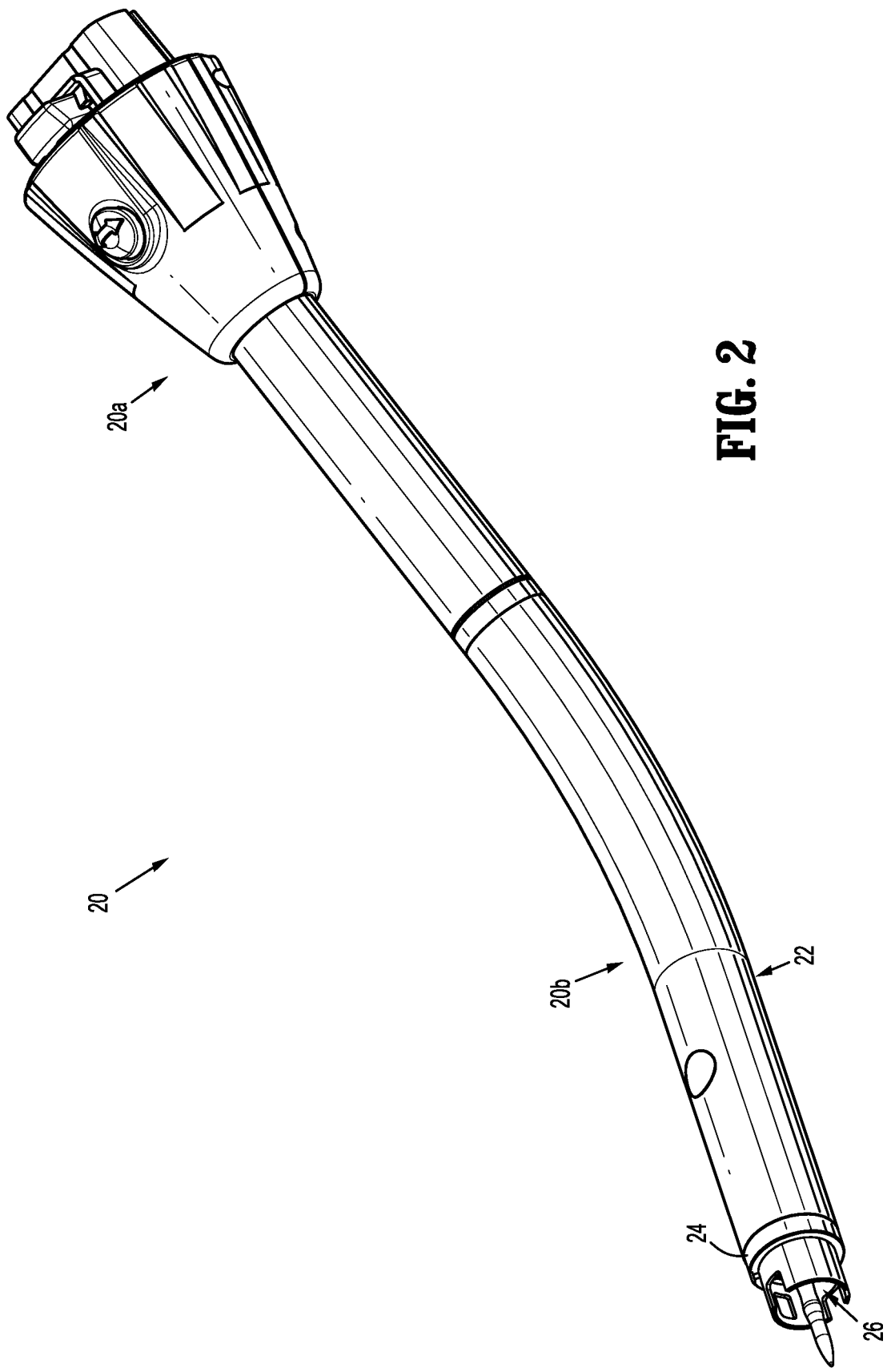
FIG. 2 is a perspective view of an adapter assembly of the surgical device of FIG. 1.

Referring now to FIG. 2, in conjunction with FIG. 1, the adapter assembly 20 includes a proximal portion 20a configured for operable connection to the handle assembly 10 (FIG. 1) and a distal portion 20b configured for operable connection to the end effector 30 (FIG. 1). The adapter assembly 20 includes an outer sleeve 22, and a distal connector housing 24 secured to a distal end of the outer sleeve 22. The distal connector housing 24 is configured to releasably secure an end effector, e.g., the end effector 30 (FIG. 1), to the adapter assembly 20.

The adapter assembly 20 will only further be described to the extent necessary to fully disclose the aspects of the present disclosure. For detailed description of an exemplary adapter assembly, reference may be made to the '157 application, the entire contents of which were previously incorporated herein by reference.

With reference now to FIG. 3A, in conjunction with FIG. 2, the adapter assembly 20 further includes a trocar assembly 26 that extends through a central aperture 101 (see e.g., FIG. 4) of a force sensor 100 and a central aperture 29 (FIG. 3B) of a trocar connection housing 28. The trocar connection housing 28 releasably secures the trocar assembly 26 relative to the outer sleeve 22 (FIG. 2) of the adapter assembly 20. For a detailed description of an exemplary trocar connection housing, reference may be made to U.S. patent application Ser. No. 14/865,602 ("the '602 application"), filed on Sep. 25, 2015, the entire contents of which are incorporated herein by reference.

Figure 5B:
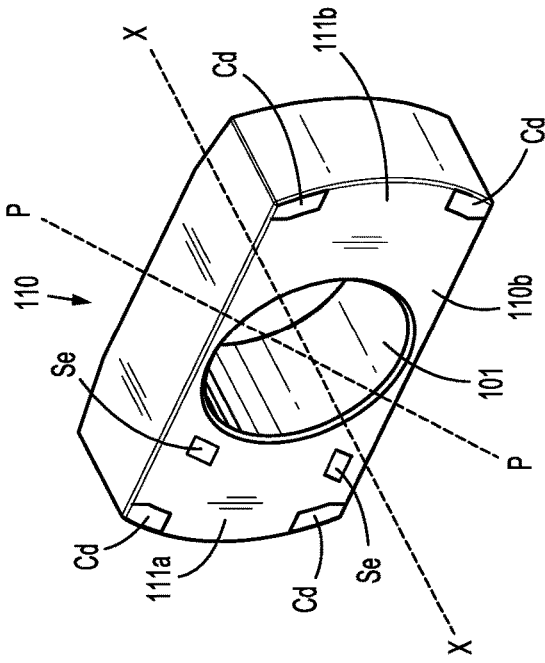
FIGS. 5A and 5B are perspective views of a substrate of the force sensor of FIG. 4.
Figure 5A:
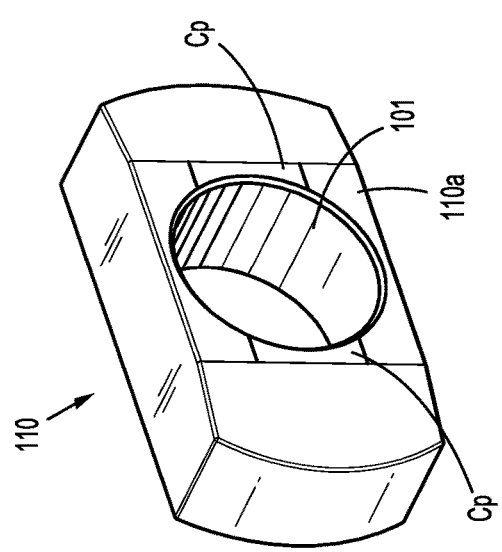

The force sensor 100 is disposed between the trocar connection housing 28 and the distal connector housing 24 of the adapter assembly 20, and is configured to measure forces along a load path. As shown in FIGS. 3B and 5A, the trocar connection housing 28 includes at least one distal surface 28a which interfaces with, and is configured to exert a load against, a proximal surface 110a of a body or substrate 110 of the force sensor 100 at proximal load contact areas "Cp". As shown in FIGS. 3C and 5B, a proximal surface 24a of the distal connector housing 24 defines contact surfaces 25 which interface with, and are configured to exert a load against, a distal surface 110b of the substrate 110 of the force sensor 100 at distal load contact areas "Cd." Thus, for example, as the anvil assembly 34 (FIG. 1) is approximated towards the loading unit 32 of the end effector 30 during clamping and/or stapling of tissue, the anvil head 34a of the anvil assembly 34 applies uniform pressure in the direction of arrow "A" (FIG. 1) against the distal end 24b of the distal connector housing 24 which, in turn, is transmitted to the distal load contact areas "Cd" of the force sensor 100.

Figure 4:
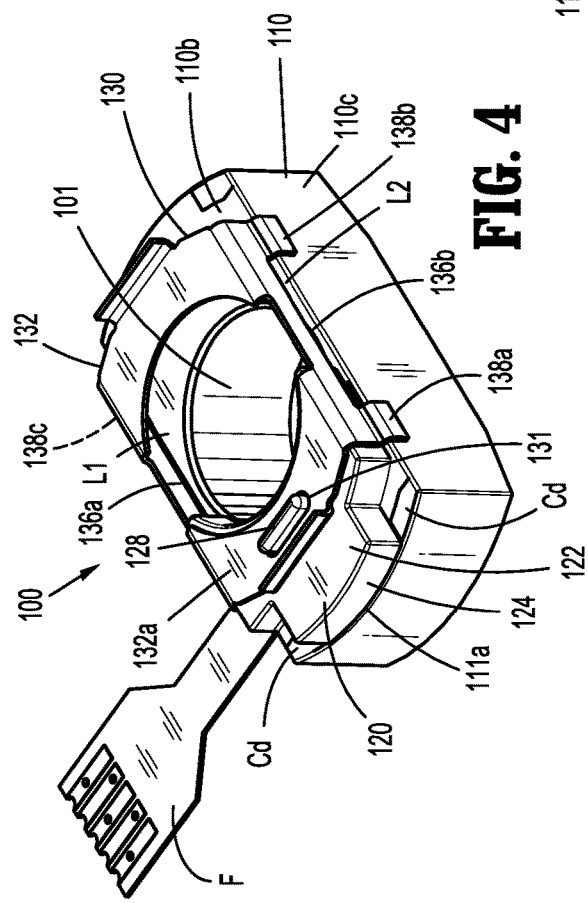
FIG. 4 is a perspective view of a force sensor of the surgical device of FIGS. 1-3A.

Referring now to FIG. 4, the force sensor 100 includes a substrate 110, at least one seal 120, and a cover plate 130. As shown in FIGS. 5A and 5B, in conjunction with FIG. 4, the substrate 110 includes a central aperture 101 defined through the proximal and distal surfaces 110a, 110b and extending along a central longitudinal axis "X" (FIG. 5B) of the substrate 110. The proximal surface 110a (FIG. 5A) and the distal surface 110b (FIG. 5B) of the substrate 110 are load bearing surfaces having proximal and distal load contact areas "Cp," "Cd," respectively, as described above, that allow the substrate 110 to flex when loaded by the surgical device 1 (FIG. 1). The distal surface 110a of the substrate 110 includes a working surface area (e.g., the remaining portion of the distal surface 110b excluding the distal load contact areas "Cd") divided into first and second lateral regions or halves 111a, 111b, by a plane "P" (FIG. 5B) intersecting the longitudinal axis "X" of the substrate 110.

As specifically shown in FIG. 5B, sensing elements "Se", for example, strain gauges, are bonded to the first lateral half 111a of the distal surface 110b of the substrate 110, along with associated components thereof (not shown), e.g., media layers, films, protective coatings, circuitry including electronic components, such as resistors, and conductive wires and/or traces, electronic and/or solder connectors, etc. The sensing elements "Se" are connected together with a series of wires or electrical conduits (not shown) to form a resistance bridge, e.g., a Wheatstone bridge, that can read a linear strain response of the substrate 110 when compressed, as is within the purview of those skilled in the art.

Figure 5E:
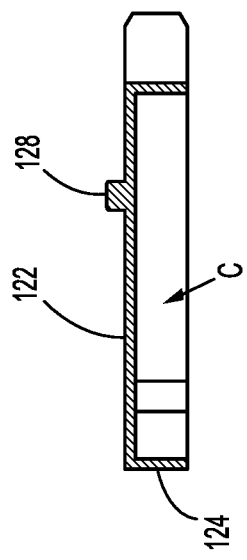
FIG. 5E is a cross-sectional view of the seal of FIGS. 5C and 5D, taken along line 5E-5E of FIG. 5C.
Figure 5D:
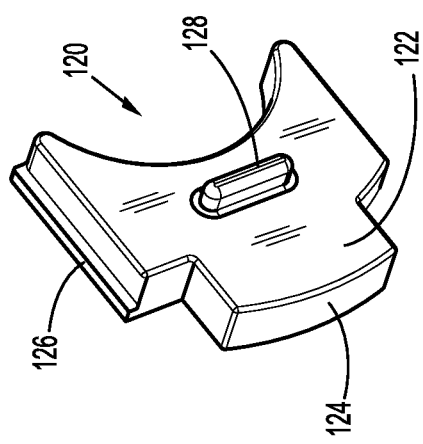
FIGS. 5C and 5D are perspective views of a seal of the force sensor of FIG. 4.
Figure 5C:
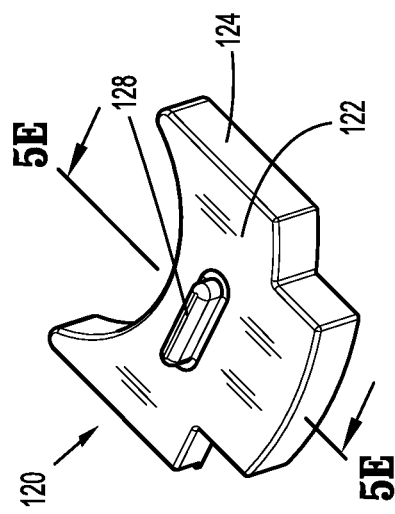

As shown in FIGS. 5C-5E, in conjunction with FIG. 4, the seal 120 of the force sensor 100 includes a substantially planar base or end wall 122 and a flange or rim 124 extending proximally therefrom and around the entire outer perimeter of the base wall 122. A lip 126 extends perpendicularly from the flange 124 along a plane parallel to a plane defined by the base wall 122 at an upper end of the seal 120. The lip 126, however, may extend at other orientations from the flange 124. The seal 120 includes a distally extending protrusion 128 disposed on the base wall 122 that is configured to mate with an opening 131 (see e.g., FIG. 5F) defined in the cover plate 130.

The seal 120 is sized and shaped to substantially cover the first lateral half 111a of the distal surface 110b of the substrate 110, leaving upper and lower, or first and second, ledges "L1," L2," respectively, (FIG. 4) on the distal surface 110b of the substrate 110 free, for seating of the cover plate 130 thereon. It should be understood that the distal load contact area "Cd" should remain uncovered and free to communicate with the distal connector housing 24 (see e.g., FIG. 3A), as described above. The flange 124 is positioned adjacent the distal surface 110b of the substrate 110 and defines a cavity "C" (FIG. 5E) between the base wall 122 of the seal 120 and the distal surface 110b of the substrate 110, providing space and clearance for the sensing elements "Se" (FIG. 5B) and associated components which are mounted on the distal surface 110b of the substrate 110, as described above.

The seal 120 may be fabricated from a low durometer material, such as silicone preferably having a durometer of 20-80. The low durometer material effectively seals the covered distal surface 110b of the substrate 110 in a fluid tight manner by a relatively low closure force provided by the cover plate 130.

Figure 5F:
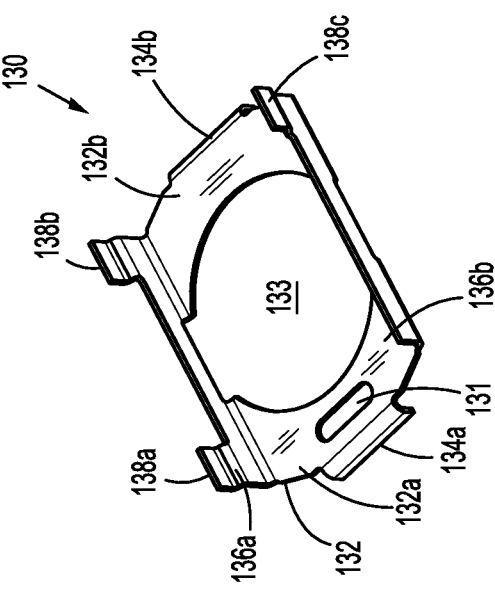
FIG. 5F is a perspective view of a cover plate of the force sensor of FIG. 4.

As shown in FIG. 5F, in conjunction with FIG. 4, the cover plate 130 of the force sensor 100 includes a plate body 132 including a central aperture 133 defined therethrough that is sized and dimensioned to be coincident with the central aperture 101 of the substrate 110. The plate body 132 has first and second lateral portions 132a, 132b that are each complementary in shape with a portion of the base wall 122 of the seal 120, and configured to abut the base wall 122 and to apply pressure onto the seal 120. One or both lateral portions 132a, 132b of the cover plate 130 may include an opening 131 defined therethrough that is configured to mate with the protrusion 128 of the seal 120, as described above. Each of the lateral portions 132a, 132b includes a distally extending projection 134a, 134b at an outer terminal end thereof that is configured to engage the distal connector housing 24 (see e.g., FIG. 6) of the adapter assembly 20.

Upper and lower, or first and second, rails 136a, 136b extend proximally from, and interconnect, the lateral portions 132a, 132b of the plate body 132. The upper and lower rails 136a, 136b are configured to be seated against the upper and lower ledges "L1," "L2" on the distal surface 110b of the substrate 110, and in embodiments in which the seal 120 includes a lip 126, to press and secure the lip 126 against the upper ledge "L1." Legs 138a, 138b extend from the upper rail 136a, and leg 138c extends from the lower rail 136b. Legs 138a-138c are configured to mate with side surfaces 100c of the substrate 110.

Figure 6:
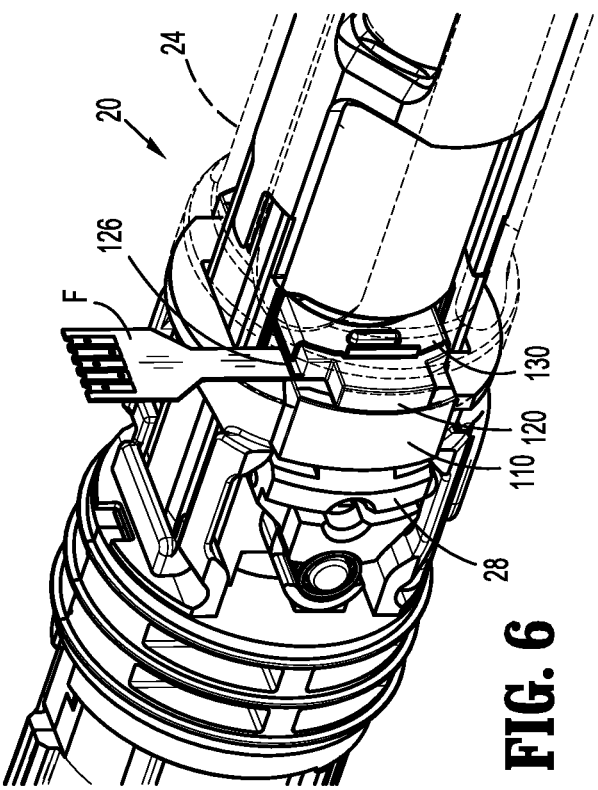
FIG. 6 is a perspective view of the distal end portion of the adapter assembly of the surgical device of FIGS. 1-3A including the force sensor of FIG. 4, with an outer sleeve of the adapter assembly removed therefrom and the distal connector housing shown in phantom.

As shown in FIGS. 4 and 6, the first lateral half 111a of the substrate 110 of the force sensor 100, which includes the sensing elements "Se" (FIG. 5B), is covered by the seal 120, with the flange 124 of the seal 120 abutting the distal surface 110b of the substrate 110. A flex cable "F," which is electrically coupled to the sensing elements, exits the force sensor 100 between the seal 120 and the distal surface 110b of the substrate 110 for electrical connection with electronics of the surgical device 1 (FIG. 1) for supplying, for example, power and reading force responses from the force sensor 100. Thus, when surgical device 1 (FIG. 1) is used in such a way to cause compression on the force sensor 100, the surgical device 1 can be programmed to perform a function with respect to the measured force.

The cover plate 130 is positioned over the seal 120 and the substrate 110 such that the protrusion 128 of the seal extends through the opening 131 in the first lateral portion 132a of the plate body 132, the upper and lower rails 136a, 136b are operably seated against or adjacent to the upper and lower ledges "L1," "L2" of the substrate 110, and the legs 138a-138c mate with the side surfaces 100c of the substrate 110.

The cover plate 130 is secured to the substrate 110 (e.g., by welding) in a manner that applies a constant pressure onto the seal 120, causing the seal 120 to firmly engage substrate 110 to prevent the ingress of fluids (e.g., gasses or liquids) during a cleaning or sterilization cycle, protecting the sensing elements and associated components from the external environment. In embodiments, the cover plate 130 is welded, for example, by laser or electronic beam welding, to the substrate 110 around the outer perimeter of the legs 138a-138c and/or the upper and lower rails 136a, 136b. The upper rail 136a of the cover plate 130 presses the lip 126 of the seal 120 into the upper ledge "L1" of the substrate 110 to ensure the seal with the distal surface 110b of the substrate 110 is not compromised by the passage of the flex cable "F" therebetween.

While the force sensor is shown including sensing elements on the first lateral half of the distal surface of the substrate, it should be understood that additionally or alternatively, the force sensor may include sensing elements on the second lateral half of the distal surface of the substrate. At least because the first and second lateral halves of the distal surface of the substrate may be mirror images of each other, a person of ordinary skill in the art will readily understand that the seal and the cover plate are each configured to accommodate such alternate or additional configurations of the sensing elements on the substrate. In embodiments in which sensing elements are disposed on each of the first and second lateral halves of the substrate, two seals would be utilized with the force sensor, as can be readily appreciated by one skilled in the art.

Referring now to FIG. 7, a force sensor 200 is shown in accordance with another embodiment of the present disclosure. The force sensor 200 is substantially the same as the force sensor 100, and therefore will only be described herein with respect to the differences therebetween. The force sensor 200 includes a substrate 210, a cover plate 130, and a reservoir plate 240.

As shown in FIG. 8A, in conjunction with FIG. 7, the substrate 210 includes a central aperture 201 defined through proximal and distal surfaces 210a, 210b of the substrate 201. The proximal surface 210a is substantially similar to the proximal surface 110a of the force sensor 100 (see e.g., FIG. 5A). The distal surface 210b is a stepped surface having first and second lateral halves 211a, 211b interconnected by an intermediate wall or shoulder 212. The first lateral half 211a of the distal surface 110a is lower than the second lateral half 211b of the distal surface 210 such that the substrate 210 has two thicknesses. In some embodiments, the first lateral half 211a is formed by removing material from the substrate 210 at a predetermined depth relative to the second lateral half 211b. In embodiments, the difference in height or thickness between the first and second lateral halves 211a, 211b is about 0.02 inches to about 0.06 inches, and in some embodiments, about 0.04 inches.

As shown in FIG. 8B, in conjunction with FIGS. 7 and 8A, the reservoir plate 240 is tiered and includes a main body 242 (e.g., a first layer of the reservoir plate 240) and a raised central portion 244 (e.g., a second layer of the reservoir plate 240). The main body 242 is sized to cover the first lateral half 211a of the distal surface 210b of the substrate 210. The main body 242 of the reservoir plate 240 has an end 242a having a complementary shape with the intermediate wall 212, and a height or thickness which is equal to the height difference between the first and second lateral halves 211a, 211b of the substrate 210. A raised central portion 244 extends distally from the main body 242 and defines an opening 243 therethrough. The first lateral half 211a provides a working surface area on which sensing elements "Se" (FIG. 5B) may be mounted, as described above with respect to the first lateral half 111a of the force sensor 100, however, the sensing elements and associated components thereof are housed within the opening 243 of the reservoir plate 240.

The reservoir plate 240 is mounted on the first lateral half 211a of the distal surface 210b of the substrate 210 over the sensing elements and a flex cable "F," with the end 242a of the reservoir plate 240 placed against the intermediate wall 212 of the substrate 210. The reservoir plate 240 is then secured to the distal surface 210b of the substrate 210 (e.g., by welding) around, for example, an entire outer perimeter of the reservoir plate 240 to hermetically seal the reservoir plate 240 to the substrate 210.

The reservoir plate 240 may be fabricated from a metal, such as stainless steel, among other materials capable of achieving a desired yield so as to bend and to allow for a responsive signal from the substrate 110 upon loading, as within the purview of those skilled in the art. The main body 242 of the reservoir plate 240 effectively removes the step between the first and second lateral halves 211a, 211b, such that the main body 242 and the second lateral half 211b of the substrate 210 are disposed at the same height. The main body 242 defines distal load contact areas "Cd" on the first lateral half 211a of the substrate 210.

The opening 243 of the reservoir plate 240 provides a cavity in which the sensing elements are protected, and may be filled with a sealant (not shown) in a fluid tight manner to hermetically seal the sensing elements and eliminate the ingress of fluids therein. The sealant may be, for example, epoxies, room-temperature-vulcanizing (RTV) sealants, urethanes, acrylics, among other materials and/or encapsulates that can withstand sterilization, disinfection, and/or cleaning procedures to which the adapter assembly 20 (FIG. 1) may be subjected, as is within the purview of those skilled in the art.

In some embodiments, a seal 120 (see e.g., FIG. 5C) may be disposed between the reservoir plate 240 and the cover 130 in addition to, or as alternative to, the use of a sealant. The cover plate 130 is disposed over the reservoir plate 240 and welded to the substrate 210 in a similar manner as described above with regard to the force sensor 100.

As shown in FIG. 9, the force sensor 200 is disposed between a trocar connection housing 28 and a distal connector housing 24 of an adapter assembly 20' of a surgical device 1 (FIG. 1) in a similar manner as force sensor 100 to measure forces along a load path and enhance control of a function of the surgical device 1, as described in further detail below.

The surgical device 1 is used, for example, in an anastomosis procedure to effect joining of two tubular or hollow tissue sections (e.g., intestinal section) together. Generally, referring again to FIG. 1, the anvil assembly 34 may be applied to the operative site either through a surgical incision or transanally and positioned within a first intestinal section (not shown) and secured temporarily thereto (e.g., by a purse string suture), and the loading unit 32 and outer sleeve 22 of the adapter assembly 20 may be inserted transanally into a second intestinal section (not shown) and secured temporarily thereto. Thereafter, a clinician maneuvers the anvil assembly 34 until the proximal end of the anvil rod 34*b* is inserted into the distal end of the adapter assembly 20, wherein mounting structure (not shown) within the distal end of adapter assembly 20 engages anvil rod 34*b* to effect mounting. The anvil assembly 34 and the loading unit 32 are then approximated to approximate the first and second intestinal sections. Surgical device 1 is then fired, ejecting staples from the loading unit 32 through the first and second intestinal sections, and a knife (not shown) cuts the portion of tissue disposed radially inward of the knife, to complete the anastomosis.

The force sensors 100, 200 of the present disclosure may be utilized to enhance the anastomosis procedure by controlling a function of the surgical device 1. For example, the force sensors may be used to control the force applied to tissue and/or rate of compression of tissue by the anvil assembly 34 and the loading unit 32. If tissue is compressed too rapidly or with too much force, it may become bruised, torn, damaged, etc. during such compression. Without being bound to any particular theory, it is believed that maintaining a constant force of compression on the tissue provides a steady yet rapid compression of tissue until the optimal staple gap is achieved for performing stapling and cutting functions. The force sensors may be utilized to first read the force to compress the tissue. Once compressed, the force sensors may also monitor the stapling function. Such monitoring allows for the programming of the stapling function. In embodiments, the surgical device is programmed to deliver a preset load or force depending on the anvil selected. For example, a smaller anvil requires a lower load or force than a larger anvil. In embodiments, the cutting function may be controlled to stop at a predetermined load or force. This allows for the electronics and software to control such functions eliminating the need for tight mechanical stops.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, the force sensors of the present disclosure may be utilized in other surgical devices, such as robotic or powered surgical devices/instruments, having a force sensor disposed therein and/or that are subject to sterilization procedures (e.g., autoclaving and/or autowashing). Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A force sensor comprising:
   a substrate including a proximal surface and a distal surface, the distal surface including first and second lateral halves;
   a plurality of sensing elements coupled to the first lateral half of the distal surface of the substrate;
   a seal sized and shaped to cover the first lateral half of the distal surface of the substrate, the seal including a base wall and a flange extending proximally from the base wall, the flange positioned against the distal surface of the substrate to define a cavity between the base wall of the seal and the distal surface of the substrate within which the plurality of sensing elements is disposed; and
   a cover plate positioned over the seal and fixed to the substrate, the cover plate including a plate body having first and second lateral portions, the first lateral portion abutting the base wall of the seal and applying a closure force on the seal to inhibit the ingress of fluids into the cavity, the cover plate including a plurality of legs engaged with side surfaces of the substrate.

2. The force sensor according to claim 1, wherein the seal is fabricated from a low durometer material.

3. The force sensor according to claim 2, wherein the seal is fabricated from silicone.

4. The force sensor according to claim 1, wherein the cover plate includes first and second rails extending from the plate body, the first and second rails operably seated adjacent first and second ledges, respectively, of the distal surface of the substrate.

5. The force sensor according to claim 4, further comprising a flex cable electrically coupled to the plurality of sensing elements and extending between the seal and the distal surface of the substrate.

6. The force sensor according to claim 4, wherein the seal includes a lip extending from the flange, the first rail of the cover plate securing the lip against the first ledge of the distal surface of the substrate.

7. The force sensor according to claim 1, wherein the seal includes a protrusion extending from the base wall of the seal, and the cover plate includes an opening, the opening in the cover plate engaged with the protrusion of the seal.

8. A surgical device comprising:
   a powered handle assembly;
   an adapter assembly including a distal connector housing and a trocar connection housing;
   an end effector releasably secured to the distal connector housing of the adapter assembly; and
   the force sensor of claim 1 disposed between the distal connector housing and the trocar connection housing, and configured to measure forces exhibited by the end effector along a load path.

9. A force sensor comprising:
   a substrate including a proximal surface and a distal surface, the distal surface including first and second lateral halves and first and second ledges;
   a plurality of sensing elements coupled to the first lateral half of the distal surface of the substrate;
   a seal sized and shaped to cover the first lateral half of the distal surface of the substrate, the seal including a base wall, a flange extending proximally from the base wall, and a lip extending from the flange, the flange positioned against the distal surface of the substrate to define a cavity between the base wall of the seal and the distal surface of the substrate within which the plurality of sensing elements is disposed; and
   a cover plate positioned over the seal and fixed to the substrate, the cover plate including a plate body having first and second lateral portions, the first lateral portion abutting the base wall of the seal and applying a closure force on the seal to inhibit the ingress of fluids into the cavity, the cover plate including first and second rails extending from the plate body, the first and second rails operably seated adjacent the first and second ledges, respectively of the distal surface of the substrate, the first rail securing the lip of the seal against the first ledge of the distal surface of the substrate.

10. The force sensor according to claim 9, wherein the seal is fabricated from a low durometer material.

11. The force sensor according to claim 10, wherein the seal is fabricated from silicone.

12. The force sensor according to claim 9, further comprising a flex cable electrically coupled to the plurality of sensing elements and extending between the seal and the distal surface of the substrate.

13. A surgical device comprising:
a powered handle assembly;
an adapter assembly including a distal connector housing and a trocar connection housing;
an end effector releasably secured to the distal connector housing of the adapter assembly; and
the force sensor of claim 9 disposed between the distal connector housing and the trocar connection housing, and configured to measure forces exhibited by the end effector along a load path.

14. A force sensor comprising:
a substrate including a proximal surface and a distal surface, the distal surface including first and second lateral halves;
a plurality of sensing elements coupled to the first lateral half of the distal surface of the substrate;
a seal sized and shaped to cover the first lateral half of the distal surface of the substrate, the seal including a base wall, a protrusion extending from the base wall, and a flange extending proximally from the base wall, the flange positioned against the distal surface of the substrate to define a cavity between the base wall of the seal and the distal surface of the substrate within which the plurality of sensing elements is disposed; and
a cover plate positioned over the seal and fixed to the substrate, the cover plate including a plate body having first and second lateral portions, the first lateral portion abutting the base wall of the seal and applying a closure force on the seal to inhibit the ingress of fluids into the cavity, the cover plate including an opening engaged with the protrusion of the seal.

15. The force sensor according to claim 14, wherein the seal is fabricated from a low durometer material.

16. The force sensor according to claim 15, wherein the seal is fabricated from silicone.

17. The force sensor according to claim 14, wherein the cover plate includes first and second rails extending from the plate body, the first and second rails operably seated adjacent first and second ledges, respectively, of the distal surface of the substrate.

18. The force sensor according to claim 14, further comprising a flex cable electrically coupled to the plurality of sensing elements and extending between the seal and the distal surface of the substrate.

19. A surgical device comprising:
a powered handle assembly;
an adapter assembly including a distal connector housing and a trocar connection housing;
an end effector releasably secured to the distal connector housing of the adapter assembly; and
the force sensor of claim 14 disposed between the distal connector housing and the trocar connection housing, and configured to measure forces exhibited by the end effector along a load path.

* * * * *